US012071608B2

(12) United States Patent
Dierker et al.

(10) Patent No.: US 12,071,608 B2
(45) Date of Patent: Aug. 27, 2024

(54) DETACHABLE DISSOLVED OXYGEN SENSOR INTERFACE FOR SINGLE-USE BIOREACTOR/MIXER

(71) Applicant: Rosemount Inc., Shakopee, MN (US)

(72) Inventors: Andrew S. Dierker, Minnetonka, MN (US); Jinbo Hu, Minneapolis, MN (US); Tyrel L. Ruch, Saint Paul, MN (US); Rick J. Sumrall, Eden Prairie (MN); Taufiq Ahmed, Apple Valley, MN (US); Ryan L. Bowlds, Chanhassen, MN (US); Michalle J. A. Adkins, Morgantown, PA (US); Marc R. Mason, Cape Coral, FL (US); John W. Simon, Burnsville, MN (US)

(73) Assignee: Rosemount Inc., Shakopee, MN (US)

( * ) Notice: Subject to any disclaimer, the term of this patent is extended or adjusted under 35 U.S.C. 154(b) by 1074 days.

(21) Appl. No.: 16/277,224

(22) Filed: Feb. 15, 2019

(65) Prior Publication Data

US 2019/0264163 A1 Aug. 29, 2019

Related U.S. Application Data

(60) Provisional application No. 62/636,408, filed on Feb. 28, 2018.

(51) Int. Cl.
*C12M 1/34* (2006.01)
*C12M 1/00* (2006.01)

(52) U.S. Cl.
CPC ............ *C12M 41/34* (2013.01); *C12M 23/28* (2013.01); *C12M 23/38* (2013.01); *C12M 41/32* (2013.01); *C12M 45/20* (2013.01)

(58) Field of Classification Search
None
See application file for complete search history.

(56) References Cited

U.S. PATENT DOCUMENTS 3,948,746 A * 4/1976 Poole ................... G01N 27/404
204/415
5,126,238 A * 6/1992 Gebhard ................ C12M 29/02
422/82.04

(Continued)

FOREIGN PATENT DOCUMENTS

CN 202117436 U 1/2012
DE 102009037345 A1 12/2010

(Continued)

OTHER PUBLICATIONS

Hasumoto et al., Use of an optical oxygen sensor to measure dissolved oxygen in seawater, 2006, Journal of Oceanography, vol. 61, pp. 99-103 (Year: 2006).*
ISO 5814, 2012, Water quality- Determination of dissolved oxygen-Electrochemical probe method. (Year: 2012).*
International Search Report and Written Opinion dated Jun. 26, 2019 for International Patent Application No. PCT/US2019/019781, 12 pages.

(Continued)

*Primary Examiner* — Holly Kipouros
(74) *Attorney, Agent, or Firm* — Christopher R. Christenson; Kelly Holt & Christenson, P.L.L.C.

(57) ABSTRACT

An interface for coupling a dissolved oxygen sensor to a single-use bioreactor container is provided. A dissolved oxygen (DO) window membrane is operably coupled to the single-use container and configured to position a DO sensor at least partially within the single-use container. In some embodiments, a DO window body mounts the DO window membrane at a distal end thereof. The DO window body can include a slide lock for facilitating positioning of a DO sensor within the DO window body. Additionally, the DO window body may include at least one heat exchange fin.

12 Claims, 6 Drawing Sheets

(56) References Cited

U.S. PATENT DOCUMENTS

| | | | |
|---|---|---|---|
| 5,456,673 | A | 10/1995 | Ziegler et al. |
| 8,640,560 | B2 | 2/2014 | Burke |
| 8,828,202 | B2 | 9/2014 | Feng |
| 2004/0027912 | A1 | 2/2004 | Bibbo et al. |
| 2007/0154353 | A1* | 7/2007 | Mitchell ............... G01N 31/225 422/82.08 |
| 2011/0236962 | A1* | 9/2011 | Loebbert ................ C12M 41/26 73/1.03 |
| 2012/0097557 | A1 | 4/2012 | Baumfalk et al. |
| 2012/0160677 | A1* | 6/2012 | Feng ...................... C12M 41/32 204/403.06 |
| 2012/0171760 | A1* | 7/2012 | Rao ........................ C12M 41/34 435/288.1 |
| 2012/0240686 | A1 | 9/2012 | Blomberg et al. |
| 2014/0144776 | A1* | 5/2014 | Wilhelm ............ G01N 27/4035 204/403.06 |
| 2014/0331795 | A1* | 11/2014 | Goodwin ................. G01K 1/14 73/864.73 |
| 2015/0204910 | A1* | 7/2015 | Chait ................ G01R 1/06788 324/750.25 |
| 2020/0333255 | A1* | 10/2020 | Reynolds ............. G01N 21/274 |

FOREIGN PATENT DOCUMENTS

| | | | |
|---|---|---|---|
| EP | 1535047 | B1 | 6/2009 |
| JP | S51-163995 | U | 12/1976 |
| JP | S63-038053 | U | 3/1998 |
| WO | 2004042870 | A2 | 5/2004 |

OTHER PUBLICATIONS

First Examination Report from Australian Patent Application No. 2019227711, dated Feb. 3, 2021, 5 pages.
Russian Search Report/ Office Action for Russian Patent Application No. 2020129830, dated Feb. 27, 2021, 12 pages including English translation.
Office Action dated Nov. 30, 2021, for Japanese Patent Application No. 2020-545098, 11 pages including English translation.
Extended Search Report dated Nov. 5, 2021 for European Patent Application No. 19760750.0, 7 pages.
First Examination Report, dated Jul. 16, 2021, for Indian Patent Application No. 202027037486, 6 pages including English translation.
Second Ofice Action for Japenese Application No. 2020-545098, daled Aug. 23, 2022, 6 pages including English translation.
First Office Action for Chinese Application No. 201980016132.4, dated Aug. 4, 2022, 19 pages including English translation.
Second Office Action for Chinese Patent App# 201980016132.4, Dated May 24, 2023, 20 pages including English Translation.
Office Action for European Patent Application No. 19760750.0, Dated Oct. 11, 2023, 5 pages.
Second Office Action for Brazilian Application No. 1120200175536, dated Mar. 26, 2024, 8 pages including English Translation.
Office Action for European Patent Application No. 19760750.0, Dated Apr. 3, 2024, 4 pages.
Rejection Decision for Chinese Application No. 2019800161324, Dated Nov. 28, 2023, 19 pages including English Translation.

* cited by examiner

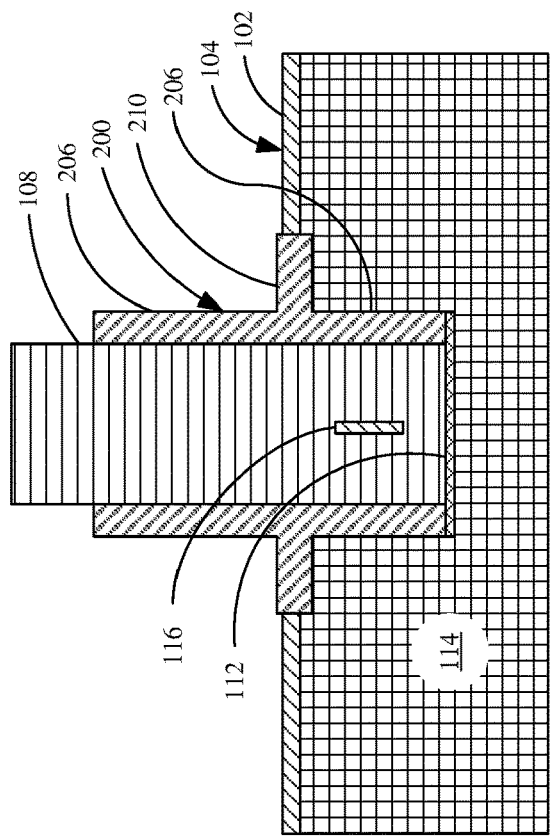
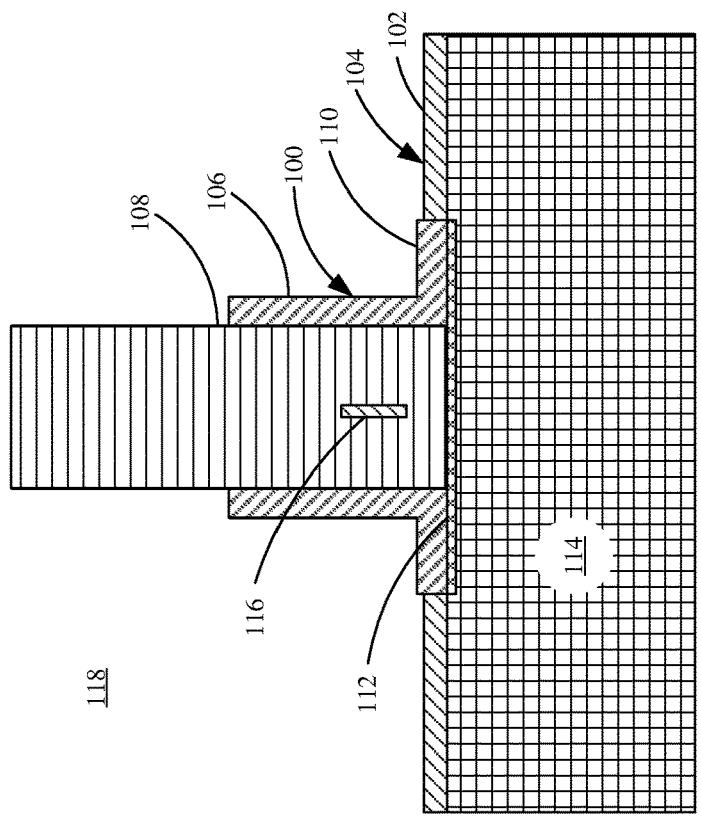
FIG. 1A
FIG. 1B

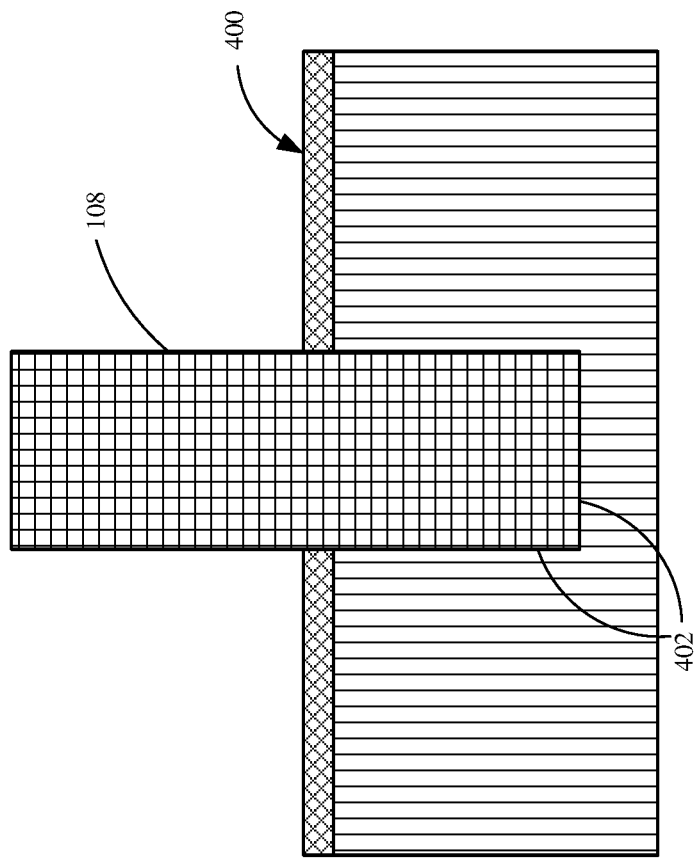
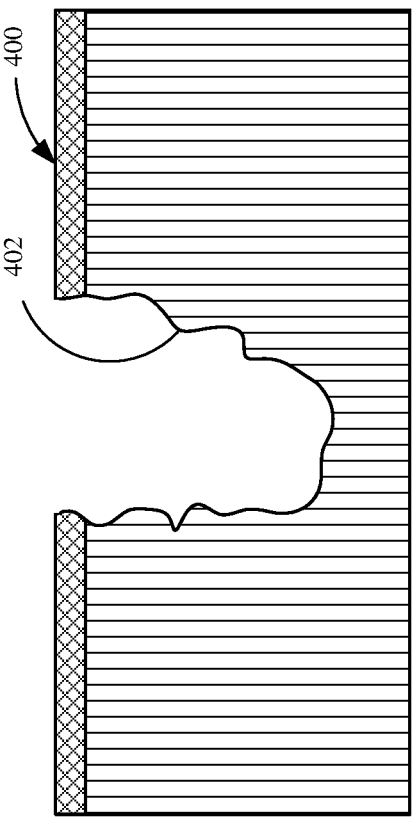
FIG. 6B
FIG. 6A

DETACHABLE DISSOLVED OXYGEN SENSOR INTERFACE FOR SINGLE-USE BIOREACTOR/MIXER

CROSS-REFERENCE TO RELATED APPLICATION

The present application is based on and claims the benefit of U.S. provisional patent application Ser. No. 62/636,408, filed Feb. 28, 2018, the content of which is hereby incorporated by reference in its entirety.

BACKGROUND

Oxygen is a gas of significant interest, simply because of its role from the cycle of all living organisms. Measurement of oxygen concentration or partial pressure is important in a wide variety of the applications. In some applications, gaseous oxygen concentrations are measured directly. In other applications, the concentration of oxygen dissolved in a liquid is measured. It is important to realize that the term "dissolved oxygen" refers to gaseous oxygen molecules dissolved in water, and it should not be confused with combined oxygen atoms as found in the water molecule, $H_2O$.

A promising application for the measurement of dissolved oxygen is in biological specimens. These biological specimens may be in vitro specimens in a laboratory, or in vivo specimens within a patient. The measurement of dissolved oxygen in biological specimens provides important diagnostic information for care providers, and/or information about the efficacy of a particular treatment. Frequently, a biological specimen is contained within a bioreactor/mixer, and the dissolved oxygen measurement provides important information about the state of the biomass contained therein.

The life sciences industry is moving away from large, capital intensive facilities made of stainless steel with large clean in place (CIP) infrastructure and toward smaller facilities utilizing polymer-based bags or containers functioning as single-use bioreactors. A single-use bioreactor bag or container can be used once and then disposed. Using single-use bioreactors can significantly reduce the capital cost required for a plant. For example, in existing facilities using stainless steel CIP infrastructure, up to 90% of operating costs may be related to CIP infrastructure, including high-end instrumentation designed to withstand a steam cleaning cycle. By moving to disposable single-use bioreactor containers, the CIP portion of capital costs can be eliminated, facilities can be flexible and much smaller, which, in turn, allows the production of smaller batches that are needed, for example, for more targeted drug therapies and other small scale applications.

A known dissolved oxygen sensor is provided in U.S. Pat. No. 8,828,202. In the design of the above-identified patent, the sensor window membrane is placed on the wall of the container and the dissolved oxygen (DO) sensor is completely outside the container. While this arrangement is useful for sensing dissolved oxygen in single-use environments, improvements can be made.

SUMMARY

An interface for coupling a dissolved oxygen sensor to a single-use bioreactor container is provided. A dissolved oxygen (DO) window membrane is operably coupled to the single-use container and configured to position a DO sensor at least partially within the single-use container. In some embodiments, a DO window body mounts the DO window membrane at a distal end thereof. The DO window body can include a slide lock for facilitating positioning of a DO sensor within the DO window body. Additionally, the DO window body may include at least one heat exchange fin.

BRIEF DESCRIPTION OF THE DRAWINGS

FIGS. 1A and 1B are diagrammatic cross section views contrasting a known design (FIG. 1A) with a design in accordance with an embodiment of the present invention (FIG. 1B).

FIGS. 6A and 6B are diagrammatic representations of interfacing a conventional DO sensor to a bioreactor container through a stretchable and elastic sensing window membrane in accordance with an embodiment of the present invention.

DETAILED DESCRIPTION OF ILLUSTRATIVE EMBODIMENTS

Figure 2B:
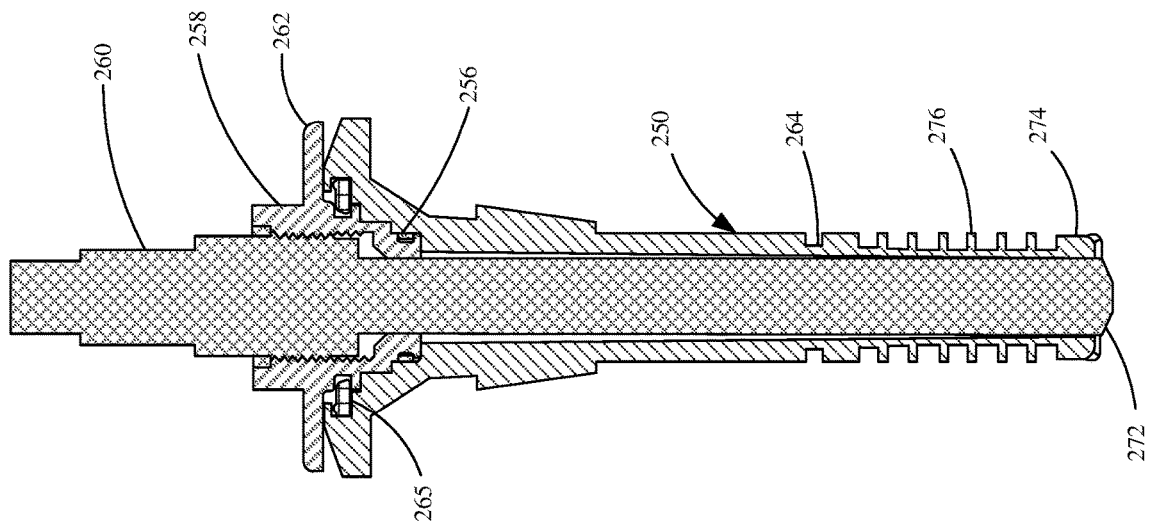
FIGS. 2A and 2B are diagrammatic elevation and cross sectional views, respectively, of a dissolved oxygen sensor in accordance with an embodiment of the present invention.

Embodiments described herein generally relate to a system and method of connecting a dissolved oxygen sensor to a single-use bioreactor container via a sensor connection window membrane and a membrane holder. This system, in one embodiment, extends the sensor connection window membrane and the dissolved oxygen sensor into the single-use bioreactor container which is believed to provide better temperature compensation. As used herein, a single-use bioreactor container is intended to encompass any container or holding vessel that is suitable for a single-use process and is discarded after use rather than reused. The preferred example is a bag having a flexible polymeric wall. Additionally, some embodiments also provide a lock mechanism to secure the dissolved oxygen sensor into the sensor window.

Temperature is an important parameter for dissolved oxygen measurements. It affects the measurement by changing the permeability of the sensor membrane and the solubility of oxygen in water. Therefore, there is an internal temperature element built in the dissolved oxygen (DO) sensor.

Known dissolved oxygen (DO) sensor designs generally provide a method to attach a DO sensor to a single-use bioreactor container via a sensor connection window membrane and a membrane holder. However, the sensor window membrane is typically located on the wall of the container and the DO sensor (and its internal temperature element) is disposed completely outside the container. This can potentially create problems in terms of temperature compensation. For a typical bioreactor container, the internal process is controlled at 36.5 C whereas the room temperature is usually 20-25 C. Therefore, there is a temperature gradient throughout the attached dissolved oxygen sensor and the temperature compensation of the dissolved oxygen sensor is not accurate. In one observation, the temperature of the bioreactor container was 36.5 C and the temperature reading of the DO sensor was only 28.1 C. This temperature discrepancy may cause significant measurement errors.

To address this problem, at least some embodiments described herein provide a sensor connection window membrane and the membrane holder that is extended into the single-use container, so that the connection window membrane, the DO sensor membrane, and the sensor internal temperature element can reach thermal equilibrium with the process. This provides a better sensor temperature compensation, thus leading to higher measuring accuracy.

FIGS. 1A and 1B are diagrammatic cross section views contrasting a known design (FIG. 1A) with a design in accordance with an embodiment of the present invention (FIG. 1B). In FIG. 1A, a known dissolved oxygen mounting system 100 is coupled to a sidewall 102 of a single-use container 104. System 100 includes a tubular sensor receiving portion 106 that is sized to receive a dissolved oxygen sensor 108. System 100 also includes a flange portion 110 that mounts to sidewall 102 of single-use container 104. Flange portion 110 also includes an oxygen permeable membrane 112 that fluidically seals the container, but otherwise allows oxygen to pass therethrough such that sensor 108 can measure the DO content of a sample 114 within container 104. For diagrammatic purposes, a temperature sensor 116 is shown within sensor 108 for compensating the DO value for temperature. However, as can be seen in FIG. 1A, temperature sensor 116 is external to container 104 and thus is susceptible to ambient temperature 118, which can cause temperature sensor 116 to read a value that is different than the temperature of sample 114 and membrane 112.

FIG. 1B is a diagrammatic view of a DO sensor holder in accordance with an embodiment of the present invention. Some of the elements shown in FIG. 1B are similar to those of FIG. 1A, and like components are numbered similarly. More particularly, it can be seen that the same DO sensor 108 that is coupled to system 100 can be coupled to dissolved oxygen sensor mounting system 200. However, system 200 mounts sensor 108 at a position that moves the sensor into container 104. System 200 includes a tubular sensor receiving sleeve or portion 206 that is sized to receive DO sensor 108. Portion 206 is coupled to flange 210 that couples to sidewall 102 of container 104. However, tubular sensor receiving portion 206 also includes a portion on the opposite side of flange 210 extending away from the interior of the container. In this way, at least a portion of tubular sensor receiving portion 206 is configured to be positioned within the container and be surrounded by sample 114. Further, temperature sensitive element 116 of sensor 108 is positioned closer to sample 114 than in mounting system 100. This helps ensure that element 116 indicates the temperature of sample 114 and/or membrane 112 more accurately.

Figure 2A:
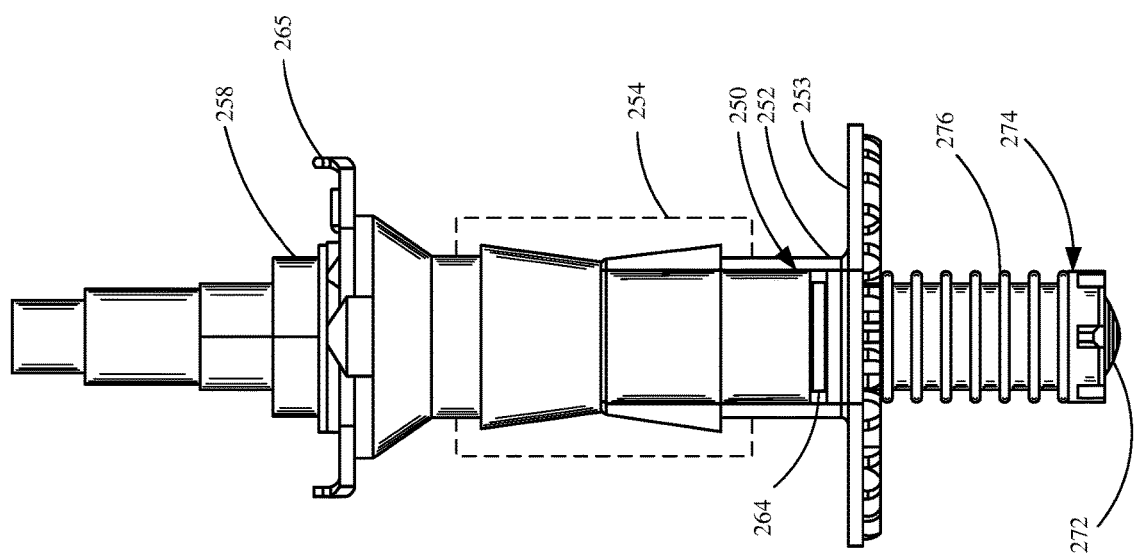

FIGS. 2A and 2B are diagrammatic elevation and cross-sectional views, respectively, of a dissolved oxygen sensor in accordance with an embodiment of the present invention. DO window body 250 is inserted into a bioreactor container flange 252, which includes a flange portion 253 that is secured and sealed to a wall of the single-use container. Window body 250 is preferably secured to bioreactor container flange 252 by elastic plastic tubing 254 (shown in phantom) covering a portion of the outside of window body 250. A seal groove 264 is configured to receive and retain an O-ring to prevent sample leakage from the single-use container. A DO sensor, which may be any suitable DO sensor now known, or later developed, is inserted into DO window body 250 and secured through sensor adaptor 258. The sensor adaptor 258 contains a thumb press 262 that facilitates insertion and alignment of DO sensor 260. In one embodiment, sensor adaptor 258 also contains a feature 265 (shown in greater detail in FIG. 3) that prevents DO sensor 260 from rotating within window body 250.

As shown in FIGS. 2A and 2B, a secondary seal element (e.g. o-ring) 256 is provided proximate the bottom of sensor adaptor 258 to prevent atmospheric oxygen from reaching down to the DO sensor tip to cause interference. The DO window membrane 272 is secured to the end of the DO window body 250 using membrane cap 274, which will be described in greater detail with respect to FIGS. 5A-5D. DO window body 250 may or may not include a plurality of heat exchange fins 276. In the illustrated embodiment, fins 276 are provided in the form of a number of annular rings encircling DO window body 250. However, it is expressly contemplated that fins 276 could additionally or alternately run longitudinally along the axis of DO window body 250. Heat exchange fins 276 are configured to be in direct contact with sample 114 and help improve heat flow to the temperature sensitive element (such as element 116) within the DO sensor.

Figure 3:
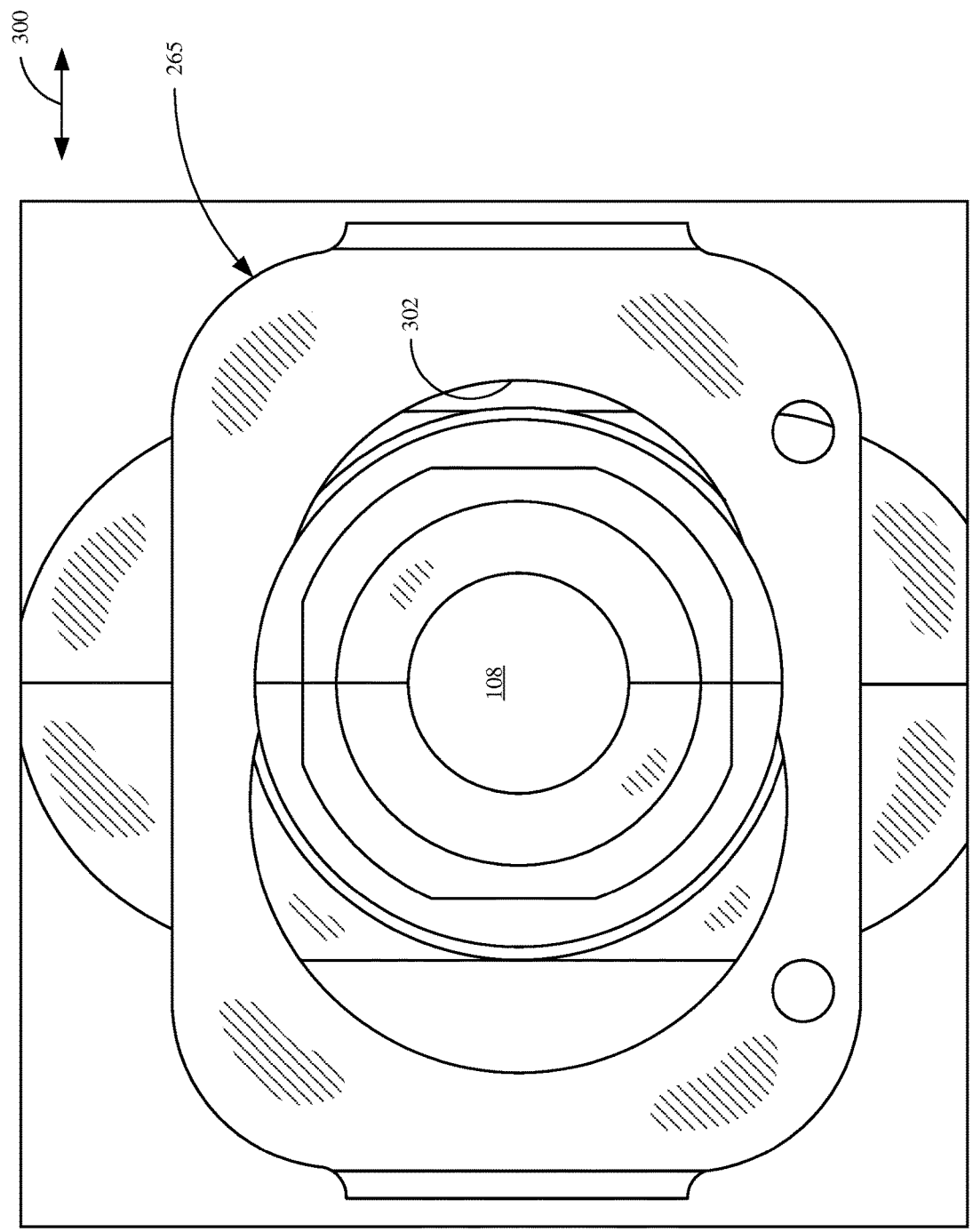
FIG. 3 is a diagrammatic top plan view illustrating a locking feature of a dissolved oxygen sensor in accordance with an embodiment of the present invention.

FIG. 3 is a diagrammatic top plan view illustrating a locking feature of a dissolved oxygen sensor in accordance with an embodiment of the present invention. Slide lock 265 is movable in the direction of arrow 300 between first and second positions. In a first position, slide lock 265 allows DO sensor 108 to be inserted or withdrawn from DO window body 250. Additionally, in the first position, DO sensor 108 can be rotated within DO window sensor body 250. However, when slide lock 265 is slid moved to the second position, a smaller diameter 302 engages a portion of DO sensor 108 and prevents axial and rotational movement. In this way, DO sensor 108 is locked in place.

Figure 4B:
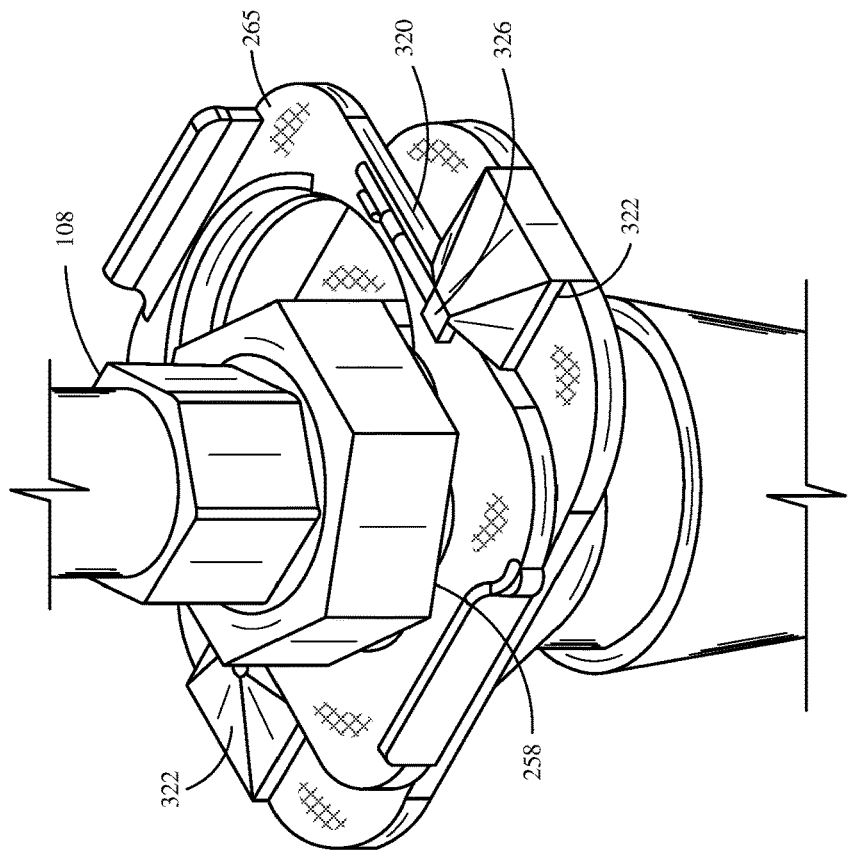
FIG. 4B is a diagrammatic view of a slide lock in use on a DO sensor in accordance with an embodiment of the present invention.
Figure 4A:
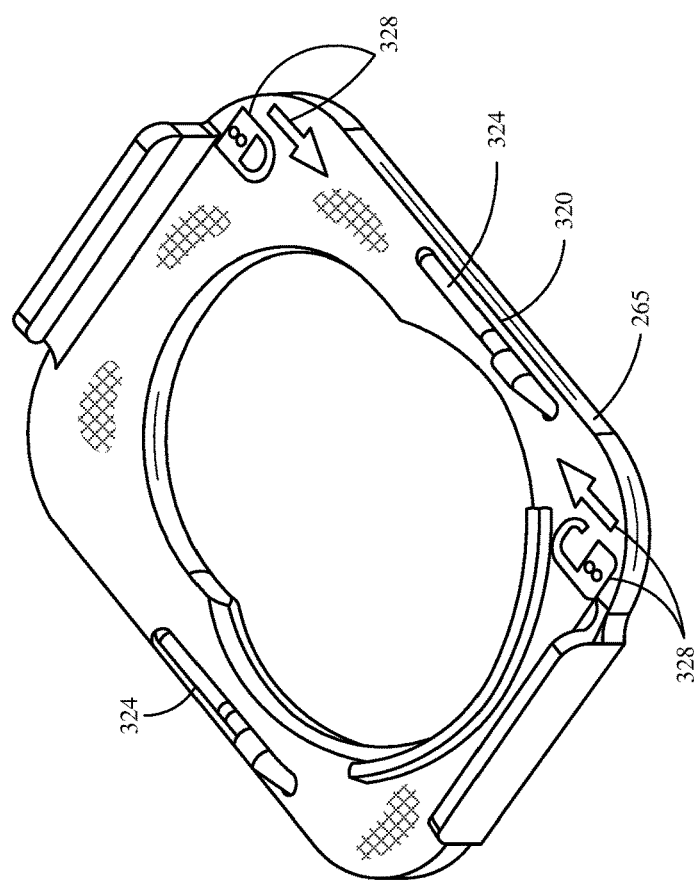
FIG. 4A is a diagrammatic view of a slide lock for a DO sensor in accordance with an embodiment of the present invention.

FIGS. 4A and 4B are diagrammatic views a slide lock for a DO sensor and a slide lock in use on a DO sensor, respectively, in accordance with an embodiment of the present invention. Slide lock 265 includes a sidewall 320 that slides within pedestals 322. The sliding motion is also constrained by ridges 324 on slide lock 265 interacting with tabs 326 of pedestals 322. Additionally, as shown in FIG. 4A, slide lock 265 may also include indicia providing a user with an indication of slide direction corresponding to locked/unlocked positions.

Slide lock 265 helps secure DO sensor 108 in place during operation and provides lockout/tagout capabilities for the end user. Lockout/tagout is a safety procedure to ensure that dangerous machines are properly shut off and not able to be started up again until completion of maintenance or repair. In this embodiment, slide lock 265 may include an aperture through which a mechanical lock is secured in order to maintain slide lock 265 in a particular orientation. When a mechanical lock is secured through the aperture in slide lock 265, slide lock 265 may not switch positions. Thus, a DO sensor may be locked in, or locked out as desired. In this way the aperture in slide lock 265 facilitates the coupling of a mechanical lock to slide lock 265 thereby facilitating lockout/tagout. Slide lock 265 also ensures that DO sensor 108 is inserted into DO window body 250 at an exact length so that the oxygen sensing tip of DO sensor 108 can properly interface with DO window membrane 272 (shown in FIGS. 2A and 2B).

Figure 5D:
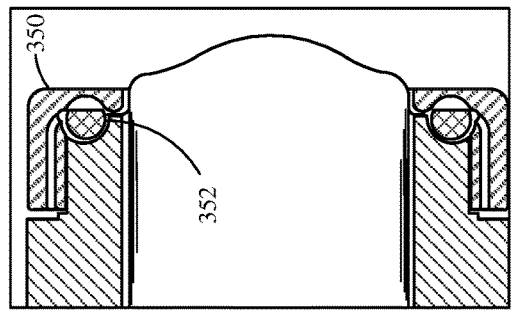
FIGS. 5A-5D are diagrammatic views of a DO membrane secured to a DO window in accordance with an embodiment of the present invention.
Figure 5C:
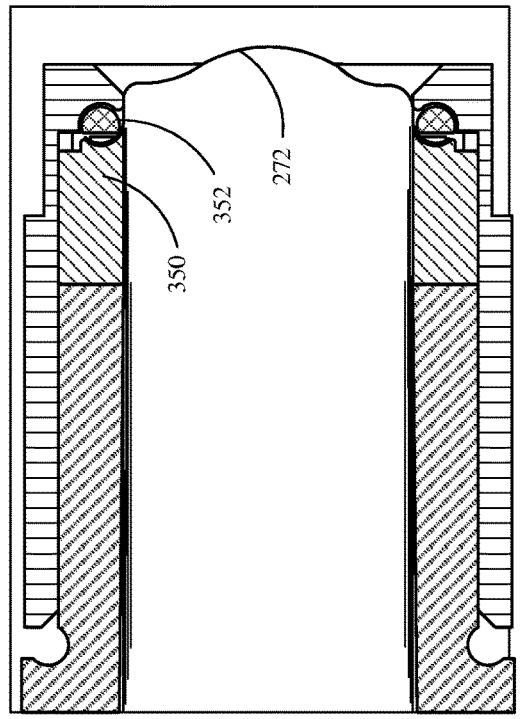
Figure 5B:
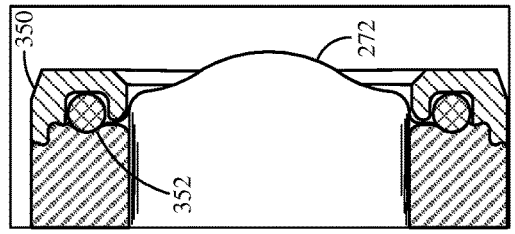
Figure 5A:
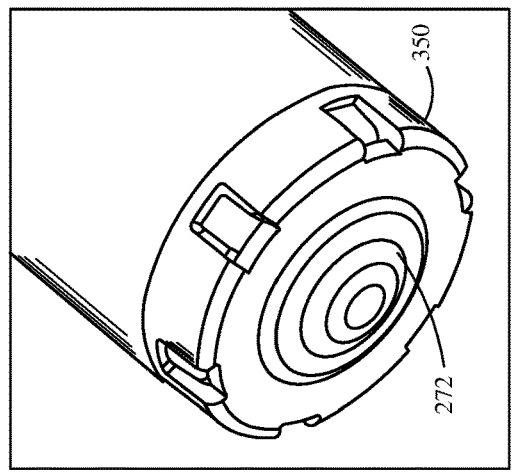

FIGS. 5A-5D are diagrammatic views of a DO membrane secured to a DO window in accordance with an embodiment of the present invention. DO window membrane 272 is secured to DO window body 250 via cap 350 being coupled to the DO window body 250. Cap 350 may be attached in any suitable manner. For example, cap 350 may be ultrasonically welded to DO window body 250 as shown in FIG. 5B. Alternatively, cap 350 may be threaded onto DO window body 250, as shown in FIG. 5C. Further, cap 350 may also be snapped onto DO window body 250 as shown in FIG. 5*d*. In all illustrated embodiments, however, an additional sealing element (o-ring 352) is compressed and seals the DO window membrane 272 and cap 350 to DO window body 250.

FIGS. 6A and 6B are diagrammatic representations of interfacing a conventional DO sensor to a bioreactor container through a stretchable and elastic sensing window membrane in accordance with an embodiment of the present invention. In accordance with another embodiment of the present invention, a stretchable, elastic sensing window membrane may be used to interface a DO sensor to the bioreactor. FIGS. 6A and 6B are diagrammatic representations of interfacing a conventional DO sensor 108 to a bioreactor container 400 through a stretchable and elastic sensing window membrane 402. In this embodiment, the DO sensor window body and cap are eliminated, but DO sensor 108 interfaces with the bioreactor container using stretchable, elastic sensing window membrane 402. When the DO sensor is not present, the membrane is in its relaxed form, but still isolates the interior of the container from the outside environment. When DO sensor 108 is placed into sensing window membrane 402 (as shown in FIG. 6B), membrane 402 will be stretched and thus wrapping around DO sensor 108, as shown. Membrane 402 is constructed from a material that renders it highly permeable to oxygen to allow oxygen from the sample/process to reach the oxygen sensing tip of DO sensor 108. However, membrane 402 is also designed (through material selection and/or thickness) to be strong and resilient enough to prevent rupturing.

As described above, embodiments described herein generally provide a DO window body, the DO membrane, and the temperature element of the DO sensor that are inserted into the container, rather than located along the wall surface of the container. Also, at least some embodiments provide fin-like features on the bottom of the DO window body to allow better heat exchange properties of the DO window body. Further, some embodiments provide a slide lock to allow selectable insertion or withdrawal of a DO oxygen sensor. Embodiments also include combinations of these features as well.

Although the present invention has been described with reference to preferred embodiments, workers skilled in the art will recognize that changes may be made in form and detail without departing from the spirit and scope of the invention. For example, a container flange could be provided where the DO sensor has a mechanical feature added to the sensor housing that interacts with the container flange. Since the container is pressurized during application, the only connection point of concern is the attachment to the container. This would eliminate plastic fastening devices (zip tie, etc.) to ensure the sensor is held in place.

What is claimed is:

1. A dissolved oxygen (DO) sensor interface system comprising:
 a single-use container having a flange that is secured and sealed to a wall of the single-use container:
 a DO window body sealingly coupled to the flange, the DO window body having DO window membrane at a distal end that extends into the single-use container;
 a sensor adaptor sealed to the DO window body; and
 a DO sensor mounted to the sensor adaptor and disposed within the DO window body, the DO sensor having a temperature sensor positioned within the single-use container and having an oxygen sensing tip positioned adjacent the DO window membrane.

2. The DO sensor interface system of claim 1, and further comprising an end cap sealingly coupling the DO window membrane to the DO window body.

3. The DO sensor interface system of claim 2, wherein the end cap is configured to couple to the DO window body via a snap operation.

4. The DO sensor interface system of claim 2, wherein the end cap is welded to the DO window body.

5. The DO sensor interface system of claim 2, wherein the end cap is configured to threadably engage the DO window body.

6. The DO sensor interface system of claim 2, and further comprising a seal ring disposed between the end cap and the DO window body to generate a fluid-tight seal.

7. The DO sensor interface system of claim 1, wherein the DO window body includes a tubular portion configured to extend into a port of the single-use container.

8. The DO sensor interface system of claim 1, wherein the DO window body includes a coupling portion having a first end and a second end, wherein the second end is disposed closer to the single-use container than the first end, the coupling portion having an outer diameter that is larger at the first end than at the second end, and wherein the outer diameter changes linearly with axial position.

9. The DO sensor interface system of claim 1, and further comprising a thumb press.

10. The DO sensor interface system of claim 9, wherein the thumb press is configured to facilitate at least one of insertion and alignment.

11. The DO sensor interface system of claim 1, wherein the adaptor includes an anti-rotation feature.

12. The DO sensor interface system of claim 1, and further comprising a movable member disposed between the DO window body and the sensor adaptor, the movable member having a first position that allows rotation of the DO sensor within the DO window body and a second position that prevents rotation of the DO sensor within the DO window body.

* * * * *